(12) United States Patent
Suzuki

(10) Patent No.: US 6,245,058 B1
(45) Date of Patent: Jun. 12, 2001

(54) APPARATUS FOR MEASURING OPTICAL CHARACTERISTIC, AN APPARATUS FOR MEASURING AN ABLATION RATE COMPRISING THE SAME, AND AN APPARATUS COMPRISING EITHER THE FORMER OR THE LATTER

(75) Inventor: Yoshitaka Suzuki, Okazaki (JP)

(73) Assignee: Nidek Co., Ltd., Aichi (JP)

( * ) Notice: Subject to any disclaimer, the term of this patent is extended or adjusted under 35 U.S.C. 154(b) by 0 days.

(21) Appl. No.: 09/177,366

(22) Filed: Oct. 23, 1998

(30) Foreign Application Priority Data

Oct. 24, 1997 (JP) .................................................... 9-309878

(51) Int. Cl.[7] .................................................... A61B 18/18
(52) U.S. Cl. .................................... 606/2; 606/4; 606/10; 606/12; 219/121.62; 356/128
(58) Field of Search .................................. 606/2, 4–6, 9, 606/10, 13, 16–18; 219/121.6, 121.67, 121.68, 121.69, 121.73, 121.74, 121.75, 121.82, 121.83, 121.85; 356/128, 388, 394, 243.1, 243.4

(56) References Cited

U.S. PATENT DOCUMENTS

| | | | |
|---|---|---|---|
| 5,261,822 | * | 11/1993 | Hall et al. . |
| 5,309,214 | * | 5/1994 | Hashimoto . |
| 5,460,627 | | 10/1995 | O'Donnell, Jr. ........................ 606/4 |
| 5,464,960 | | 11/1995 | Hall et al. ........................ 219/121.6 |
| 5,507,799 | | 4/1996 | Sumiya . |
| 5,520,679 | * | 5/1996 | Lin . |
| 5,523,543 | * | 6/1996 | Hunter, Jr. et al. . |
| 5,562,656 | | 10/1996 | Sumiya . |
| 5,624,436 | | 4/1997 | Nakamura et al. . |
| 5,633,708 | * | 5/1997 | Svendsen . |
| 5,637,109 | | 6/1997 | Sumiya . |
| 5,772,656 | * | 6/1998 | Klopotek . |
| 5,800,424 | * | 9/1998 | Sumiya . |

* cited by examiner

Primary Examiner—John P. Leubecker
Assistant Examiner—Ahmed Farah
(74) Attorney, Agent, or Firm—Finnegan, Henderson, Farabow, Garrett & Dunner, L.L.P.

(57) ABSTRACT

An apparatus for measuring an optical characteristic of an ablation standard object having a known ablation rate, as compared with an object to be processed having a unknown ablation rate which is ablated with laser beam, the apparatus comprising a retaining device for retaining the ablation standard object so that a surface thereof may be at the predetermined height, a refractive power measuring device for measuring a refractive power of the ablation standard object, which includes a projecting optical system for projecting target luminous flux for use in refractive power measurement onto the ablation standard object retained by the retaining device and a detecting optical system for detecting the target luminous flux projected by the projecting optical system, a moving device for moving the refractive power measuring device to the predetermined measuring position in order to measure the refractive power of the ablation standard object, and an output device for outputting results measured by the refractive power measuring device.

17 Claims, 6 Drawing Sheets

APPARATUS FOR MEASURING OPTICAL CHARACTERISTIC, AN APPARATUS FOR MEASURING AN ABLATION RATE COMPRISING THE SAME, AND AN APPARATUS COMPRISING EITHER THE FORMER OR THE LATTER

BACKGROUND OF THE INVENTION

1. Field of the Invention

The present invention relates to an apparatus for measuring optical characteristic of an ablation standard object ablated with laser beam, an apparatus for measuring an ablation rate comprising the same, and an apparatus comprising either the former or the latter.

2. Description of Related Art

A well known processing apparatus ablates an object with laser beam. The processing apparatus ablates a corneal surface with excimer laser beam, thereby causing its curvature to change in order to correct ametropia of an eyeball.

When an excimer laser works successively under the condition that the fixed processing condition is given, an ablation depth per one shot, at the time of irradiating the same object to be processed, is considered approximately constant. (Where the ablation depth is referred to as "ablation rate", in the description, and one shot is referred to as "one scan" in the preferred embodiment.) However, the ablation rate often changes due to a kind of object to be processed, timing when the laser works, some factors such as output energy of the laser and the processing condition, and the like. The change of the ablation rate exerts a bad influence upon an apparatus such as to need accurate depth control, particularly upon an apparatus such as to ablate a cornea to form it into the desired and fixed shape. However, it is difficult to obtain an actual ablation rate of the cornea.

Therefore, the present applicant has been proposed an apparatus in U.S. Pat. No. 5,624,436 corresponding to Japanese Patent application laid-open No. HEI6(1994)-226471, by which the operator can easily obtain an ablation rate, the apparatus correcting based on the ablation rate. The apparatus disclosed in the publication ablates an ablation standard object having a known ablation rate (a transparent plate made from PMMA (polymethyl methacrylate)), where an ablation rate of an object (a cornea) is unknown, in order to form the ablation standard object into such a curved surface as to have the desired optical characteristic. Next, the operator measures the optical characteristic of the curved surface actually formed on the standard object with a measuring means (a lens_meter). The operator then inputs the measured data into the apparatus, then causing the apparatus to calculate the ablation rate of the object to be processed in a manner of comparing the desired optical characteristic with the actual optical characteristic, thereby correcting a driving information of the apparatus.

However, referring to above mentioned method, the operator causes the apparatus to ablate the standard object and then has to move the standard object from the ablation apparatus to a lens_meter commonly on sale in order to measure the object. It is troublesome for the operator and takes a lot of time. Accuracy of the measured results tend to be easily and subtly influenced by alignment of the standard object relative to a measuring optical system of the lens_meter and an operator's skill and knowledge for operating the same.

Further, in the case that the operator reads and inputs the results measured by the lens_meter into the ablation apparatus by using input means such as a keyboard and the like, there are possibility of artificial mistakes in reading and inputting the measured results. Input operation is also troublesome for the operator and takes a lot of time.

SUMMARY OF THE INVENTION

The present invention has been made in view of the above circumstances and has an object to overcome the above problems and to provide an apparatus by which an operator can measure accurately and easily optical characteristic after ablating without moving an ablation standard object. Another object of the present invention is to provide an apparatus which does not make the operator feel troublesome in operation and to provide an apparatus by which the artificial mistakes can be reduced.

To achieve the objects and in accordance with the purpose of the present invention, as embodied and broadly described herein, an apparatus for measuring an optical characteristic of an ablation standard object having a known ablation rate, as compared with an object to be processed having a unknown ablation rate which is ablated with laser beam, the apparatus comprises retaining means for retaining the ablation standard object so that a surface thereof may be at a predetermined height, refractive power measuring means for measuring a refractive power of the ablation standard object, which includes a projecting optical system for projecting target luminous flux for use in refractive power measurement onto the ablation standard object retained by the retaining means and a detecting optical system for detecting the target luminous flux projected by the projecting optical system, moving means for moving the refractive power measuring means to the predetermined measuring position in order to measure the refractive power of the ablation standard object, and output means for outputting results measured by the refractive power measuring means.

Another aspect of the present invention, the apparatus for measuring an ablation rate of an ablation apparatus which ablates an object to be processed with laser beam, the apparatus comprises retaining means for retaining an ablation standard object having a known ablation rate, as compared with said object to be processed having a unknown ablation rate, so that a surface of the ablation standard object may be at the predetermined height, refractive power measuring means for measuring a refractive power of the ablation standard object, which includes a projecting optical system for projecting target luminous flux for use in refractive power measurement onto the ablation standard object retained by the retaining means and a detecting optical system for detecting the target luminous flux projected by the projecting optical system, moving means for moving the refractive power measuring means to the predetermined measuring position in order to measure the refractive power of the ablation standard object, calculating means for calculating an ablation rate and/or its changing ratio based on results measured by the refractive power measuring means, and output means for outputting results obtained by the calculating means.

Further another aspect of the present invention, an ablation apparatus comprising laser irradiating means for irradiating with laser beam by which an object to be processed is ablated, the apparatus comprises retaining means for retaining an ablation standard object having a known ablation rate, as compared with said object to be processed having a unknown ablation rate, so that a surface of the ablation standard object may be at the predetermined height, refractive power measuring means for measuring a refractive power of the ablation standard object, which includes a projecting optical system for projecting target luminous flux for use in refractive power measurement onto the ablation standard object retained by the retaining means and a detecting optical system for detecting the target luminous flux projected by the projecting optical system, moving means for moving the refractive power measuring means to the predetermined measuring position in order to measure the refractive power of the ablation standard object, and correcting means for correcting a driving information of the laser irradiating means at the time of irradiating the object to be processed with laser beam based on results measured by the refractive power measuring means.

According to the present invention, an operator can measure accurately and easily optical characteristic after ablating without moving an ablation standard object for use in calibration. The measured results can be inputted automatically into the ablation apparatus. Accordingly, the operator does not feel troublesome in operation and the artificial mistakes can be reduced.

BRIEF DESCRIPTION OF THE DRAWINGS

The accompanying drawings, which are incorporated in and constitute a part of this specification, illustrate embodiments of the present invention and, together with the description, serve to explain the objects, advantages and principles of the invention. In the drawings.

DETAILED DESCRIPTION OF THE PREFERRED EMBODIMENTS

Figure 1:
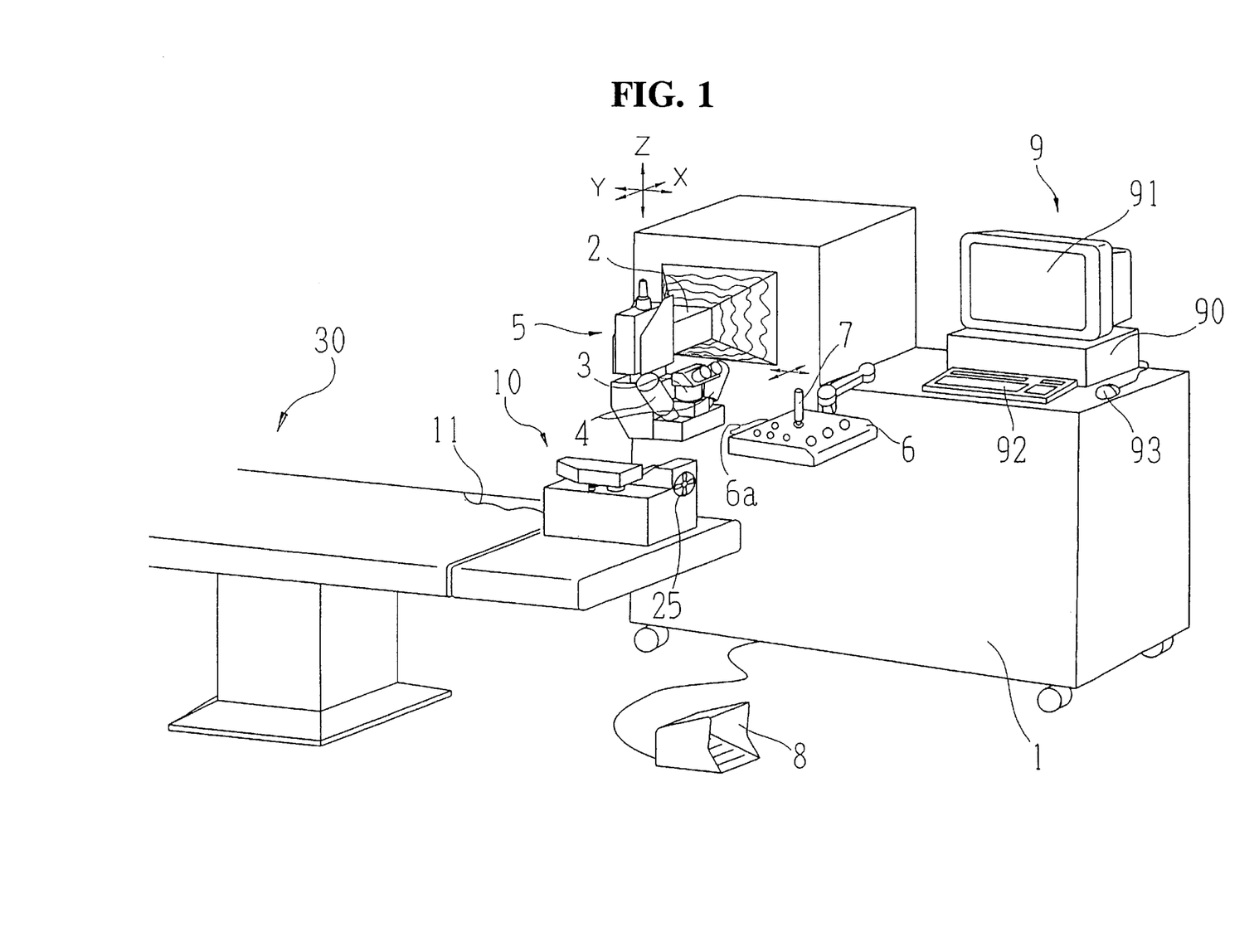
FIG. 1 is an external view showing an ablation apparatus according to the preferred embodiment of the present invention.

A detailed description of one preferred embodiment of the present invention will now be given referring to the accompanying drawings. FIG. 1 is an external view showing an ablation apparatus which corrects ametropia of a cornea with laser beam. Numeral 1 denotes a surgery apparatus in which an excimer laser source and the like are installed. Laser beam from the excimer laser source passes through below mentioned laser irradiating optical system of the apparatus 1, thus being guided to an arm 2. The arm 2 includes an optical path for guiding laser beam at which optical elements such as mirror and the like are arranged. An arm end 5 of the arm 2 is provided with a binocular microscope 3 for observing a patient's eye, an illumination part 4, and a nozzle (not shown) for emitting laser beam. A driving device (not shown) allows the arm 2 to move to XY directions, the arm end 5 to move to Z direction.

Numeral 6 denotes a controller which includes a joystick 7 which outputs a signal to allow the arm 2 to move to XY directions, a switch 6a which is utilized for bringing into focus while aligning in Z direction, and the like. Numeral 8 denotes a foot switch which is utilized for sending a laser irradiation signal. Numeral 9 denotes a computer which is utilized for inputting respective kinds of data such as conditions necessary for surgery, for calculating a laser irradiation data, for displaying and storing the same and the like. The computer 9 includes a main frame 90, a monitor 91, a keyboard 92, a mouse 93 and the like.

Numeral 10 denotes a calibration unit, details of which is described below. The calibration unit 10, prior to ablating a cornea, ablates a transparent plate made from PMMA which has known relation to the corneal ablation rate. The calibration unit 10 then measures a refractive power of the transparent plate, sending the measured results to the computer 9 automatically via a connecting cable 11. The surgery apparatus 1 (the computer 9), based on the sent data, performs calibration with the same laser output energy as corneal ablation. In preferred embodiment as shown in FIG. 1, when using the calibration unit 10, it is arranged on a bed 30 on which the patient is laid down so as to be within a moving range of the arm end 5. Alternatively, it may specially arranged on an exclusive table.

Figure 2:
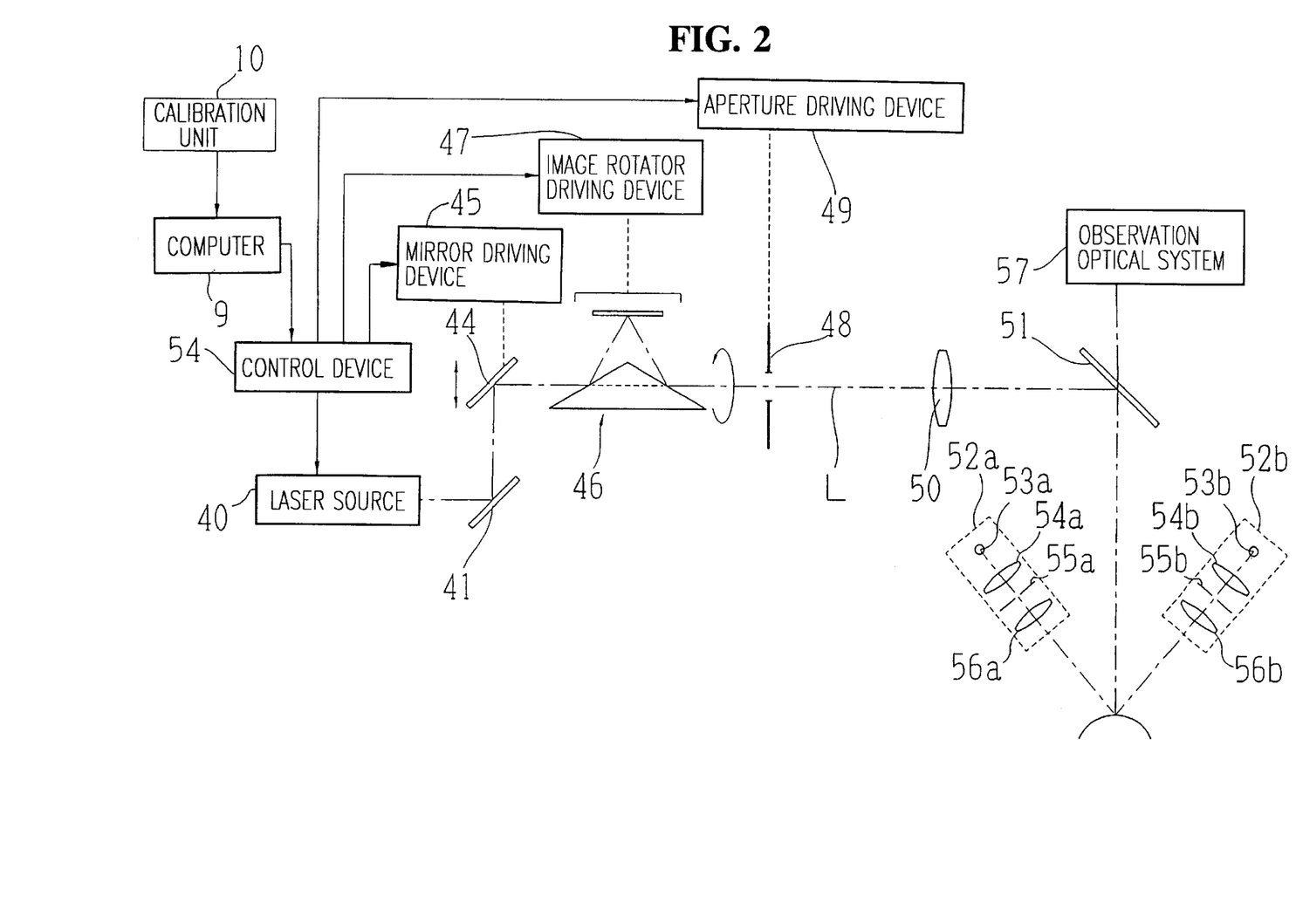
FIG. 2 is a view showing a schematic arrangement of an optical system and a schematic construction of a control system of an ablation apparatus of a preferred embodiment of the present invention.

Next, a schematic arrangement of an optical system and a schematic construction of a control system of the surgery apparatus 1 will be described referring to FIG. 2. Numeral 40 denotes a laser source which emits excimer laser having wavelength of 193 nm. Laser beam emitted from the laser source 40 is deflected 90° upwardly by a plane mirror 41, then being deflected to a horizontal direction once more by a plane mirror 44. A mirror driving device 45 allows the plane mirror 44 to move to a vertical direction (a direction denoted by an allow). By making a parallel translation of the laser beam in the direction of Gaussian distribution, the object can be ablated uniformly. In this respect, details are disclosed in U.S. Pat. No. 5,507,799 corresponding to Japanese Patent application laid-open No. HEI4(1992)-242644.

Numeral 46 denotes an image rotator which is rotated by an image rotator driving device 47 with the center at an optical axis L, thus causing the laser beam to rotate around the optical axis L. Numeral 48 denotes a variable circular aperture of which a diameter can be variable by an aperture driving device 49. Numeral 50 denotes a projecting lens which is utilized for projecting the aperture 48 onto the cornea of the eye to be ablated (during correction, substitute object is located). The aperture 48 and the cornea are conjugate with respect to the projecting lens 50. The area restricted by the aperture 48 forms images on the cornea, thus restricting the area to be ablated.

Numeral 51 denotes a dichloic mirror having such characteristic that reflects excimer laser beam having wavelength of 193 nm and transmits visible light. Laser beam via the projecting lens 50 is deflected 90° by the dichloic mirror 51, then being guided to the cornea.

Numerals 52a and 52b denote symmetric slit projecting optical systems arranged in the illumination part 4. Respective slit projecting optical systems 52a and 52b include illumination lumps 53a and 53b, condenser lenses 54a and 54b, slit plates 55a and 55b having cross slits, and projecting lenses 56a and 56b. Respective slit plates 55a and 55b and the cornea are conjugate with respect to the projecting lenses 56a and 56b, so that images of the cross slits may form images at a focusing position on the optical axis of an observation optical system 57 located above the dichloic mirror 51. The preferred embodiment may adopt such unit as being on the market for an observation optical system, details of which has little relation to the present invention, thus being omitted.

Numeral 54 is a control device which controls whole of the apparatus, thus controlling the laser source 40, the mirror driving device 45, the image rotator driving device 47, the aperture driving device 49 and the like.

Figure 3:
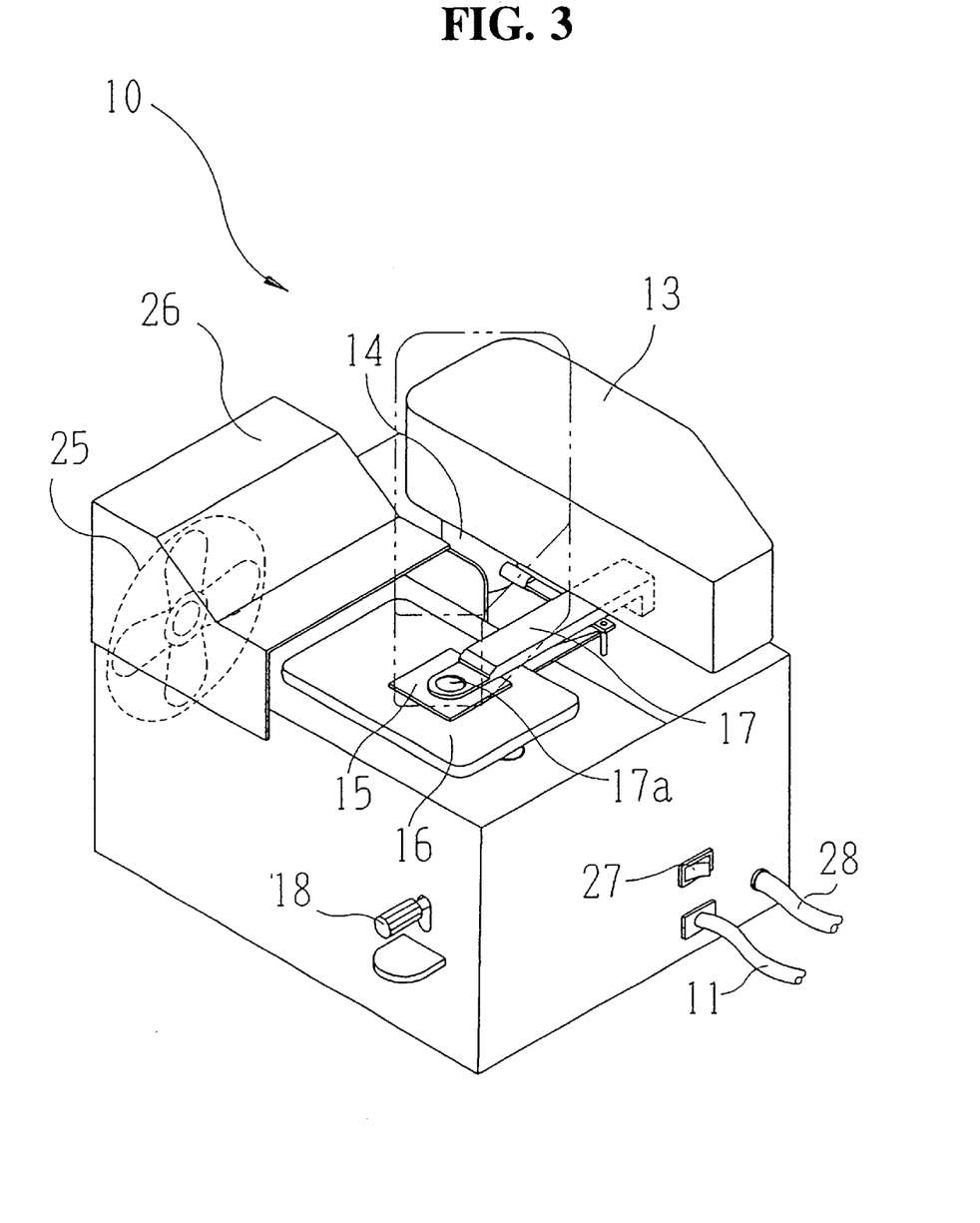
FIG. 3 is an external view showing a calibration unit of a preferred embodiment of the present invention.
Figure 4:
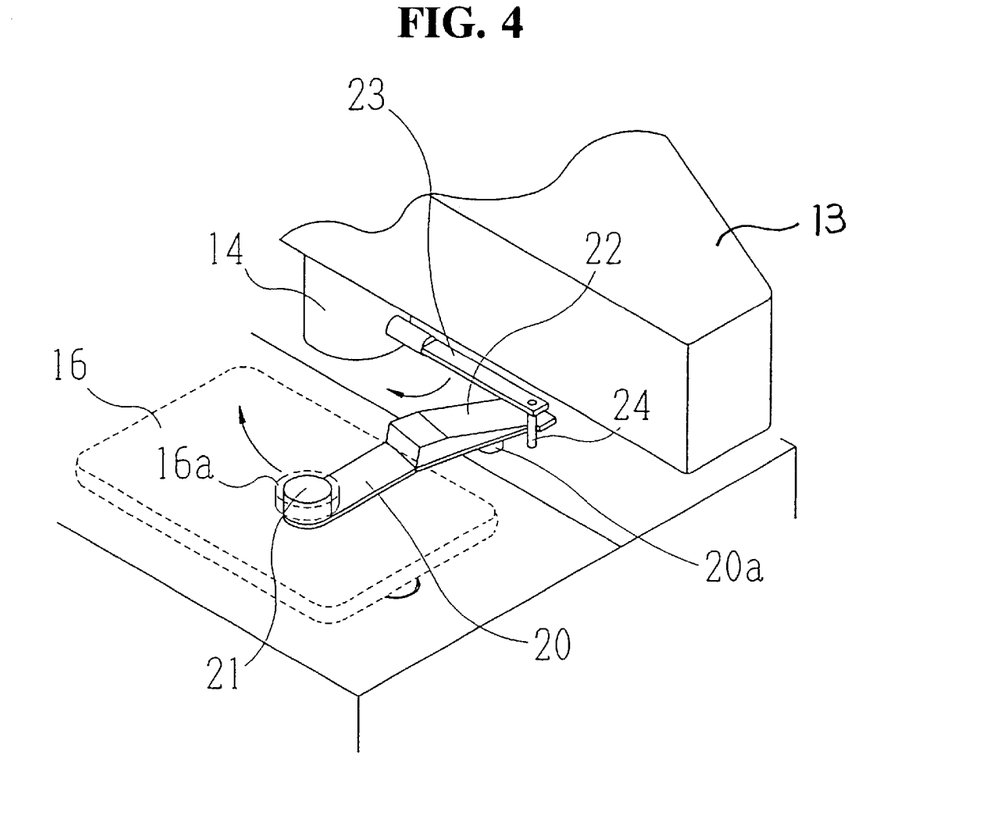
FIG. 4 is a view for illustrating mechanism for driving a standard stage of a calibration unit.

Next, construction of the calibration unit 10 will be described referring to FIGS. 3, 4 and 5. FIG. 3 is a view for illustrating external construction of the calibration unit 10. The calibration unit 10 stores a projecting optical system of a measuring optical system mentioned below, and the rotation casing 13 disposed at upper part of the unit 10 stores a receiving optical system of the measuring optical system. The rotation casing 13 is carried on the rotation shaft 14 so as to rotate pivotally between a stowed position denoted by solid lines and a measuring position denoted by dotted lines.

The transparent plate 15 made from PMMA for use in calibration is fixed by a stand 16 and a holder plate 17. One end of the holder plate 17 is fixed to the unit 10, the other end thereof being provided with a circular aperture 17a for passing (irradiating) laser beam from the surgery apparatus 1. The stand 16 is always forced upwardly by a carrying shaft and a spring disposed at underside of the stand 16. By pushing a lever 18 downwardly, the stand 16 can be moved downwardly. The stand 16 is also provided with an aperture 16a (see FIGS. 4 and 5) at a position corresponding to the aperture 17a of the holder plate 17, through which a measuring light from the projecting optical system can pass.

In addition, in the case of aligning the transparent plate 15 in order to perform a laser irradiation, reflection of both surfaces of the plate 15 makes difficult to be aligned accurately. Thus, prior to putting the transparent plate 15 on the stand 16, it is preferable that the alignment has been completed for the laser irradiation. For the purpose, as shown in FIG. 4, a standard stage 21 is arranged at the aperture 16a at the time of aligning. In FIG. 4, an actuating plate 20 is pivotally mounted with the center at the rotation shaft 20a carried on the unit 10, being forced upwardly. A circular standard stage 21, being a little smaller than the aperture 16a of the stand 16, is mounted on one end of the actuating plate 20, the height of which is set as the same as thickness of the stand 16. The height of upper surface of the standard stage 21 is set so as to be the same as the height of upper surface of the stand 16, where upper surface of the actuating plate 20 touches lower surface of the stand 16. An inclined block 22 is mounted on a part of the actuating plate 20 where is not laid on the stand 16. On the contrary, a support rod 23 is fixed to the rotation shaft 14 on which the rotation casing 13 is mounted, and a pin 24 extending downwardly is mounted on one end of the support rod 23. By causing the rotation casing 13 to move from the stowed position to the measuring position, the support rod 23 rotates simultaneously. The support rod 23 pivotally rotates along the inclined surface of the inclined block 22, causing the actuating plate 20 to move downwardly. That causes the standard stage 21 to be out of the aperture 16a of the stand 16. Simultaneously, a pin 24, mounted on one end of the support rod 23, rolls smoothly along both side face of the actuating plate 20 and that of the inclined block 22, thereby causing the actuating plate 20 to rotate pivotally with the center at the rotation shaft 20a, further causing the standard stage 21 to be out of the optical path. That allows measurement to be performed smoothly.

In FIG. 3, numeral 25 denotes a blast fan which dust smoke produced by irradiating the transparent plate 15 with laser beam. Numeral 26 denotes a fan cover by which wind is sent to the transparent plate 15 efficiently. Numeral 27 denotes a power switch, 28 denotes a power source code.

Figure 5:
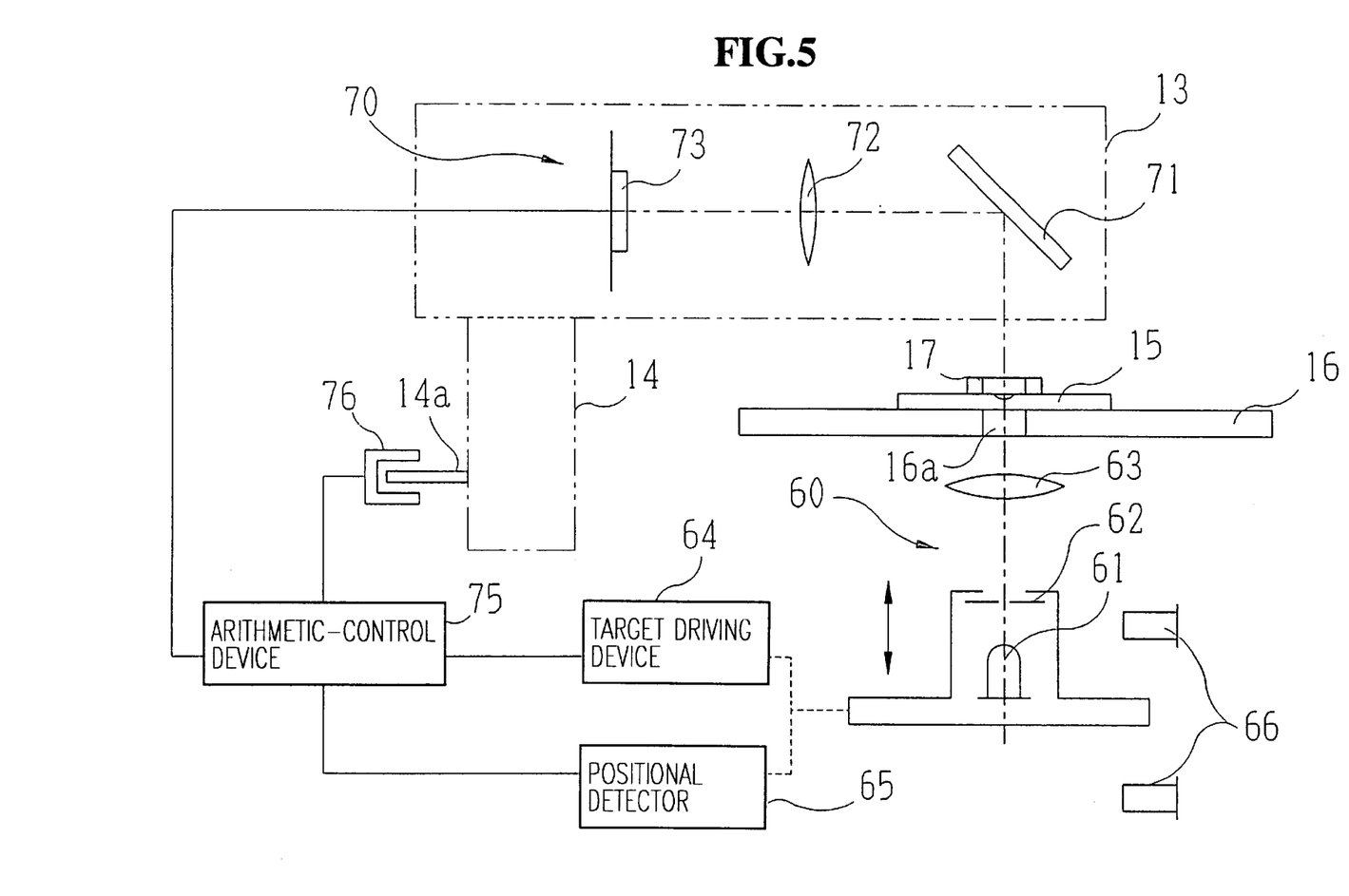
FIG. 5 is a view showing a schematic arrangement of an optical system and a schematic construction of a control system of a calibration unit.

FIG. 5 is a view for illustrating a measuring optical system and a control system of the calibration unit 10.

Numeral 60 denotes a projecting optical system, 61 denotes a LED for light projection, 62 denotes a target plate for measurement having a spot aperture, and 63 denotes a collimating lens. A back focal point of the collimating lens 63 substantially coincides with lower surface of the holder plate 17. A target driving device 64 allows the LED 61 and the target plate 62 to move in a body upwardly and downwardly (in the direction of the measuring optical axis), the moved position is then detected by the positional detector 65. Numeral 66 denotes a limit sensor which detects a moving limit to which the target plate 62 can move. Numeral 70 denotes a receiving optical system which is disposed inside the rotation casing 13, including a mirror 71, an objective lens 72, a photodetector 73, such as a CCD, and the like. Numeral 75 denotes an arithmetic-control device which drives the target driving device 64 based on a signal from the photodetector 73 and obtains a positional signal from the positional detector 65, thereby calculating a refractive power of the transparent plate 15. Numeral 76 denotes a light intercepting sensor which detects whether the rotation casing 13 (the receiving optical system 70) is arranged at the measuring position or not, in a manner of detecting a light intercepting plate 14a fixed to the rotation shaft 14.

Next the measurement of the refractive power, which is performed by the calibration unit 10 having above mentioned architecture will be described hereinafter. When the light intercepting sensor 76 detects that the receiving optical system 70 is arranged at the measuring position, the arithmetic-control device 75 then causes the LED 61 to be turned on and starts measuring. Measuring light from the LED 61 illuminates the measuring target (the spot aperture) of the target plate 62. In the initial condition, the target plate 62 is located at the conjugate position relative to the photodetector 73. The target luminous flux from the target plate 62 forms an image on the photodetector 73 via the collimating lens 63, the ablated transparent plate 15, the mirror 71, and the objective lens 72. In the case that the transparent plate 15 has a refractive power, the target image on the photodetector 73 is blurred. Therefore the arithmetic-control device 75 drives the target driving device 64 thereby causing the target plate 62 to be moved so that the target image may become smallest (the target plate 62 may be at conjugate position relative to the photodetector 73). By obtaining the moving position detected by the positional detector 65, the refractive power of the transparent plate 15 can be calculated.

Next, correction for change of the ablation rate by using a corneal ablation apparatus having above mentioned architecture will be described hereinafter.

The operator sets the laser irradiation mode to the calibration mode with the keyboard 92 of the computer 9, then inputting conditions such as a desired refractive power of an artificial lens (lens surface), an ablation range and the like. The operator puts the calibration unit 10 on the bed 30 or the like, so that the unit 10 may be within a range in which the arm end 5 can move. The operator performs alignment as follows. The operator operates the joystick 7 so that the aperture 17a of the end of the holder plate 17 may be located at the center of the visual field with observing the observation optical system 57 in the binocular microscope 3, causing the arm end 5 to move. In the case that the rotation casing 13 of the calibration unit 10 is at the stowed position, according to the above construction, the standard stage 21 is arranged at the aperture 16a of the stand 16, the height of which is the same as the height of lower surface of the holder plate 17. The operator causes the arm end 5 to move so that the cross slit image, from the illumination part 4, for use in alignment may be within the standard stage 21 of the aperture 16*a*. The operator then performs the alignment in XY directions so that the cross slit image may be located at the center of the aperture 16*a*. In the case of the alignment in Z direction (the focusing direction), the cross slit image which separates laterally is adjusted so as to be single image.

When the alignment is completed, the operator pushes the lever 18, causing the stand 16 to move downwardly, then putting the transparent plate 15 on the stand 16, which is made from PMMA being a standard object for rate, and putting it between the holder plate 17 and the stand 16 not to move. Accordingly, the laser is aimed at upper surface of the transparent plate 15.

After preparing the transparent plate 15, the ablation is performed by way of irradiating with laser beam. Based on the laser irradiation condition, the control device 54 drives the plane mirror 44, the aperture 48 and the image rotator 46 via each driving device, and the laser irradiation causes the transparent plate 15 to be formed into a curved surface (spherical surface or aspherical surface). During ablation, smoke (removed trash) is produced, but it can be removed in a manner of driving the blast fan 25. Therefore it is restrained from being influenced by such factor that causes the ablation rate to change. The blast fan 25 starts working when the operator operates the computer 9 and sets it to the calibration mode. Alternatively, the blast fan 25 may be configured so as to start working when the power switch 27 of the calibration unit 10 is turned on.

After completing the ablation of the transparent plate 15, the refractive power of the lens surface which is actually made is measured. By causing the rotation casing 13 to move from the stowed position to the measuring position, the standard stage 21 is out of the measuring optical path and the light intercepting sensor 76 detects that the receiving optical system 70 is arranged at the measuring position, thereby the measurement being performed automatically. During the measurement, the target plate 62 moves to the direction where depends on the desired refractive power of the artificial lens (lens surface), inputted by the operator. The arithmetic-control device 75 measures the refractive power of the lens surface formed on the transparent plate 15 as described above. As described, with leaving a condition as it is, the measurement of the ablation standard object on which a lens surface is formed can be performed easily without moving the standard object after ablation. In addition, since another alignment is not needed in order to perform the measurement, accurate measured results can be obtained with avoiding influence due to the alignment displacement.

The measured value obtained by the arithmetic-control device 75 is read by the computer 9 via the cable 11. The computer 9 compares the desired refractive power, which is inputted, with the actual refractive power, then calculating the changing rate of the refractive powers and the changing rate of the ablation rate based on the changing rate of the refractive powers, thereby correcting the driving information of the ablation apparatus.

Figure 6:
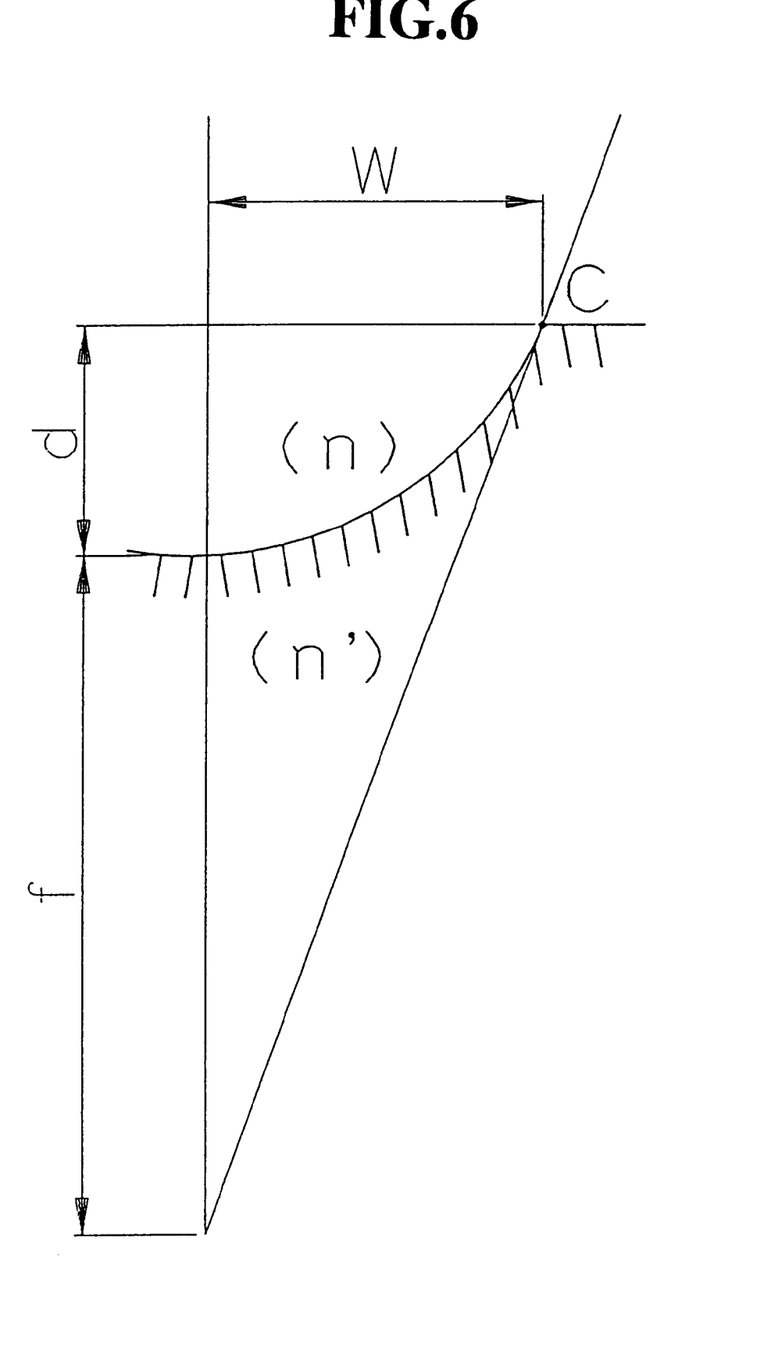
FIG. 6 is a view for illustrating effect to the refractive power due to change of an ablation rate.

Herein, referring to FIG. 6, the relationship between a lens surface formed on the transparent plate 15 by ablating and a refractive power thereof will be described. Generally, it is assumed that a refractive index of medium A is "n", the same of medium B is "n'", and the boundary between the mediums A and B is aspherical lens surface (in the preferred embodiment, the medium A is air, the medium B is PMMA). The ablation depth "d" and the diameter "w" at any point C on the aspherical lens surface satisfy the following relationship equation.

$$w^2 = \frac{\{(n^2 - n'^2)d^2 + 2n'(n-n')fd\}}{n'^2}$$

Where f is a focal distance. The boundary surface formed by the ablation apparatus of the preferred embodiment is strictly in the shape of stairs. However, it is defined as an aspherical lens, thus allowing the measuring optical system in the calibration unit 10 to measure it with defining as a lens surface.

Accordingly, the ablation depth d is defined as a product of an ablation rate multiplied by an integer and the aperture 48 is adjusted so that the diameter w of a projected image thereof at each depth d may satisfy the above relationship equation, thereby allowing the transparent plate 15 to be formed into a lens surface. If the ablation rate equals to a standard value (set value), a lens surface with an arbitrary focal distance f can be produced in such an easy method of controlling the aperture 48 so as to satisfy above relationship equation. On the contrary, in the case where the transparent plate 15 is processed under the condition that the actual ablation rate is out of the standard value, the change of the lens power of a formed lens can be calculated as followings. If the above relationship equation is rewritten to another equation for lens power D (1/f), the following equation (1) is given:

$$D = \frac{2n'(n-n')d}{n'^2w^2 - (n^2-n'^2)d^2} \tag{1}$$

If the width w is defined so as to be much larger than the depth d, then $n'^2w^2$ is much larger than $(n^2-n'^2)$. A reasonable approximation for the equation (1) is given by the following equation (2).

$$D = \frac{2n'(n-n')}{n'^2w^2}d \tag{2}$$

As shown by the equation (2), the lens power D is in direct proportion to the ablation depth d, resulting that the changing rate of the ablation rate equals to that of the lens power. Therefore, the ablation rate of the present time can be obtained in a manner of measuring the refractive power of the lens surface formed on the transparent plate 15 and then comparing the measured value with the refractive power formed when the ablation rate is the standard value.

The ablation rate at the present time is obtained, the ablation apparatus then adjusts a laser output energy from the laser source 40, thereby correcting the ablation rate. Alternatively, the correction can also be carried out as follows. In the case where a diameter of the aperture 48 can be expressed as a function of an ablation depth as described above, a diameter of each aperture 48, being a product of the ablation rate multiplied by an integer, is calculated to control the aperture 48 based on the calculated results. In the case of shotting laser pulses repeatedly until the predetermined depth, the numbers of pulses are controlled by way of dividing the processing depth by the ablation rate.

The ablation rate is corrected by the apparatus, preferably, the transparent plate 15 is then ablated repeatedly under the calibration mode, and it is confirmed whether the transparent plate 15 can be ablated in accordance with a desired refractive power. If needed, after aligning, another part of the transparent plate 15 is irradiated to form a lens surface thereon. The measurement is then carried out automatically in a manner of allowing the rotation casing 13 of the calibration unit 10 to rotate to the measuring position, then the data being inputted into the computer 9.

In the case of actual surgery upon a cornea, the operator operates the computer 9, setting the laser irradiation mode to the surgery mode, inputting data necessary for correcting ametropia, aligning the apparatus with the cornea, thereby allowing the apparatus to ablate the cornea.

The present invention is not restricted to above mentioned preferred embodiment. For example, referring to the preferred embodiment, the rotation casing 13 of the calibration unit 10 is made to rotate manually. Alternatively, the apparatus may be provided with a driving unit or the like, so that the rotation casing 13 may be made to rotate automatically as soon as the ablation is finished. In addition, referring to the preferred embodiment, the projecting optical system 60 is stored inside the calibration unit 10 and the receiving optical system 70 is stored inside the rotation casing 13. Alternatively, the receiving optical system 70 may be stored inside the calibration unit 10, and the projecting optical system 60 may be stored inside the rotation casing 13.

What is claimed is:

1. An apparatus for measuring an optical characteristic of an ablation standard object having a known ablation rate, the apparatus comprising:

refractive power measuring means for measuring a refractive power of an ablation standard object, which includes a measuring optical system having a projecting optical system for projecting target luminous flux for use in refractive power measurement onto said ablation standard object and a detecting optical system for detecting said target luminous flux projected by said projecting optical system;

a first casing and a second casing storing said measuring optical system divided thereinto, wherein said first casing stores part of said measurement optical system fixedly disposed therein and is provided with an aperture though which said target luminous flux passes and said second casing is supported by said first casing and moved from a stowed position to a predetermined measuring position at the time of measurement of said refractive power;

retaining means for retaining said ablation standard object placed on said first casing at a predetermined height; and output means for outputting the refractive power of said ablation standard object measured by said refractive power measuring means, said ablation standard object having been ablated to form a spherical surface thereon.

2. The apparatus for measuring an optical characteristic according to claim 1, further comprising:

dusting means for dusting trash removed during ablation, which is produced at the time of ablating said ablation standard object.

3. The apparatus for measuring an optical characteristic according to claim 1, wherein said first casing stores one of said projecting optical system and said detecting optical system.

4. The apparatus for measuring an optical characteristic according to claim 1, wherein said second casing stores one of said projecting optical system and said detecting optical system.

5. The apparatus for measuring an optical characteristic according to claim 1, further comprising:

detecting means for detecting whether said second casing is moved to the predetermined measuring position; and instructing means for instructing said refractive power measuring means to start measurement based on a result detected by said detecting means.

6. The apparatus for measuring an optical characteristic according to claim 1, wherein said refractive power measuring means further comprises:

projecting optical system moving means for moving said projecting optical system on a measuring optical axis;

positional detecting means for detecting a position to which said projecting optical system is made to move by said projecting optical system moving means; and calculating means for calculating a refractive power of said ablation standard object based on a result detected by said positional detecting means.

7. The apparatus for measuring an optical characteristic according to claim 1, wherein said projecting optical system includes a spot target utilized for projecting target luminous flux for measuring the refractive power.

8. The apparatus for measuring an optical characteristic according to claim 1, further comprising:

moving means for moving said second casing from the stowed position to the predetermined measuring position;

judging means for judging whether said ablation standard object is ablated or not; and control means for controlling said moving means so that said second casing may move to the predetermined measuring position based on a result judged by said judging means.

9. The apparatus for measuring an optical characteristic according to claim 1, further comprising:

an alignment standard stage which is utilized for aligning a laser irradiating axis of an ablation apparatus for ablating an object to be processed with a laser beam in a direction of two or three dimension, wherein said alignment standard stage is moved in accordance with movement of said second casing.

10. The apparatus for measuring an optical characteristic according to claim 1, wherein the refractive power of said ablation standard object outputted by said output means is utilized for obtaining at least either an ablation rate of an ablation apparatus for ablating an object to be processed with a laser beam or a changing ratio of the ablation rate, said ablation apparatus having a laser source for emitting the laser beam.

11. The apparatus for measuring an optical characteristic according to claim 1, wherein the refractive power of said ablation standard object outputted by said output means is utilized for calibrating driving information of laser beam irradiating means included in an ablation apparatus for ablating an object to be processed with laser beam, said laser beam irradiating means comprising a laser source for emitting a laser beam and an irradiation optical system for directing the emitted laser beam.

12. The apparatus for measuring an optical characteristic according to claim 1, wherein said ablation standard object includes a transparent plate made from polymethyl methacrylate (PMMA).

13. An apparatus for measuring an ablation rate of an ablation apparatus which ablates an object to be processed with laser beam, the apparatus comprising:

retaining means for retaining an ablation standard object having a known ablation rate, as compared with said object to be processed having an unknown ablation rate, so that a surface of said ablation standard object may be at a predetermined height;

refractive power measuring means for measuring a refractive power of said ablation standard object, which includes a measuring optical system having a projecting optical system for projecting target luminous flux for use in refractive power measurement onto said ablation standard object retained by said retaining means and a detecting optical system for detecting said target luminous flux projected by said projecting optical system, wherein part of said measuring optical system is moved from a stowed position to a predetermined measuring position at the time of measurement;

calculating means for calculating at least either an ablation rate or a changing ratio of the ablation rate based on the refractive power of said ablation standard object measured by said refractive power measuring means, said ablation standard object having been ablated to form a spherical surface thereon; and output means for outputting a result obtained by said calculating means.

14. The apparatus for measuring an ablation rate according to claim 13, wherein the result outputted by said output means is utilized for calibrating driving information of laser beam irradiating means included in the ablation apparatus, said laser beam irradiating means comprising a laser source for emitting a laser beam and an irradiation optical system for directing the emitted laser beam.

15. A calibration unit for a laser processing apparatus causing ablation, the calibration unit comprising:

a plate for calibration having a known ablation rate in relation to an object to be processed through ablation caused by said laser processing apparatus;

a measuring optical system for measuring a refractive power of said plate, which includes a projecting optical system for projecting a target luminous flux for use in refractive power measurement onto said plate and a detecting optical system for detecting the projected target luminous flux;

a first casing and a second casing storing said measuring optical system divided thereinto, wherein said first casing stores part of said measuring optical system fixedly disposed therein and is provided with an aperture through which the target luminous flux passes and said second casing is supported by said first casing and moved from a stowed position to a predetermined measuring position at the time of measurement;

retaining means for retaining said plate placed on said first casing at a predetermined height; and output means for outputting the refractive power of said plate measured by said measuring optical system, said plate having been ablated to form a spherical surface thereon.

16. The calibration unit according to claim 15 wherein the refractive power of said plate outputted by said output means is utilized to obtain at least either an ablation rate of said laser processing apparatus or a changing ratio of the ablation rate, said laser processing apparatus having a laser source for emitting a laser beam.

17. The calibration unit according to claim 15 , wherein the refractive power of said plate outputted by said output means is utilized for calibrating driving information of a laser beam irradiating means included in said laser processing apparatus, said laser beam irradiating means comprising a laser source for emitting a laser beam and an irradiation optical system for directing the emitted laser beam.

* * * * *